(12) United States Patent
Fabbri (10) Patent No.: US 10,232,069 B2
(45) Date of Patent: Mar. 19, 2019

(54) STERILIZATION MACHINE FOR REPROCESSING AN ENDOSCOPE

(71) Applicant: STEELCO SPA, Riese Pio X (IT)

(72) Inventor: Andrea Fabbri, Mezzano (IT)

(73) Assignee: STEELCO SPA, Riese Pio X (IT)

( * ) Notice: Subject to any disclaimer, the term of this patent is extended or adjusted under 35 U.S.C. 154(b) by 584 days.

(21) Appl. No.: 14/653,454

(22) PCT Filed: Dec. 18, 2013

(86) PCT No.: PCT/IB2013/061107
§ 371 (c)(1),
(2) Date: Jun. 18, 2015

(87) PCT Pub. No.: WO2014/097189
PCT Pub. Date: Jun. 26, 2014

(65) Prior Publication Data
US 2015/0306264 A1    Oct. 29, 2015

(30) Foreign Application Priority Data
Dec. 18, 2012    (IT) ................ B02012A0678

(51) Int. Cl.
*A61L 2/00*    (2006.01)
*B08B 3/00*    (2006.01)
(Continued)

(52) U.S. Cl.
CPC .............. *A61L 2/18* (2013.01); *A61B 1/123* (2013.01); *A61B 1/125* (2013.01); *A61B 90/70* (2016.02);
(Continued)

(58) Field of Classification Search
CPC ........... A61L 2/00; A61B 1/005; A61B 90/70; A61M 25/00
(Continued)

(56) References Cited

U.S. PATENT DOCUMENTS 5,279,799 A    1/1994 Moser
2003/0190256 A1*    10/2003 Halstead ................ A61B 1/123
422/28

FOREIGN PATENT DOCUMENTS

EP    1 477 106 A1    11/2004
EP    1 696 969 A1    9/2006
(Continued)

OTHER PUBLICATIONS

Search Report and Written Opinion for PCT/IB2013/061107, dated Mar. 24, 2013.

*Primary Examiner* — Monzer R Chorbaji
(74) *Attorney, Agent, or Firm* — Marshall, Gerstein & Borun LLP (57) ABSTRACT

Sterilization machine for reprocessing an endoscope comprising a fixed part and a mobile part. The fixed part comprises a first frame and a first fluid-dynamic circuit for feeding and/or discharging fluids, and provided with a plurality of first connectors. The mobile part comprises a second frame on which a tank is mounted, a lid to hermetically close the tank and a second fluid-dynamic circuit connectable to the endoscope, able to be selectively coupled removably with the first connectors to achieve the fluidic communication with the first fluid-dynamic circuit. The second frame is provided with rolling means, and the first frame and the second frame comprise guide means and anchoring means to removably anchor the first frame to the second frame.

12 Claims, 4 Drawing Sheets

(51) Int. Cl.
  *E03B 11/00* (2006.01)
  *A61L 2/18* (2006.01)
  *A61L 2/26* (2006.01)
  *A61B 1/12* (2006.01)
  *A61L 2/20* (2006.01)
  *A61B 90/70* (2016.01)

(52) U.S. Cl.
  CPC .......................... *A61L 2/20* (2013.01); *A61L 2/26* (2013.01); *A61B 2090/701* (2016.02); *A61L 2202/17* (2013.01); *A61L 2202/24* (2013.01)

(58) Field of Classification Search
  USPC ..... 422/292, 297, 300–301; 134/166 R, 200; 137/255, 265, 316, 383, 572, 576, 590
  See application file for complete search history.

(56) References Cited

FOREIGN PATENT DOCUMENTS

EP            1 905 343 A1      4/2008
WO      WO-03/084578 A1      10/2003

\* cited by examiner fig. 1 fig. 3 fig. 2 fig. 4 fig. 5 fig. 6 fig. 7 fig. 8

STERILIZATION MACHINE FOR REPROCESSING AN ENDOSCOPE

FIELD OF THE INVENTION

The present invention is applied in the technical field relating to sterilization machines for reprocessing rigid and flexible endoscopes previously used on patients. The reprocessing process can comprise washing and sterilizing an endoscope.

BACKGROUND OF THE INVENTION

Document EP-B-1.696.969 describes an apparatus for reprocessing endoscopes equipped with several channels held together by a sheath.

In its essential components, the apparatus comprises a machine and a small case.

The machine is provided with a hydraulic circuit and with means for the controlled injection into the hydraulic circuit of fluids, such as washing liquids, sterilization liquids, flushing gases and gases to verify the seal.

The washing and sterilization liquids, and gases to flush the liquids and to verify the seal must be applied on the various compartments of the endoscope to be reprocessed or along the channels or in the volume defined between sheath and channels.

The case is provided with a containing body in which the endoscope is put, and with a closing lid that hermetically closes the containing body. When the lid is put to close the containing body, it forms a chamber to receive an endoscope to be reprocessed.

The case is also provided with connectors equipped with safety valves that allow to put the chamber in communication with the outside.

In particular, the case can comprise connectors to couple in airtight manner with each channel of the endoscope, at least one connector to couple in airtight manner with the volume comprised between sheath and channels of the endoscope and at least one connector communicating with the chamber.

The machine comprises a seating to receive the case and connectors for the hydraulic circuit disposed in the seating.

Sliding guides are also provided in the machine, and are disposed in the seating, to allow the guided insertion of the case into the seating.

The sliding guides also allow to achieve the connection of the connectors of the case with the connectors of the hydraulic circuit, thus putting the hydraulic circuit in fluidic connection with the chamber and the channels of the endoscope. When the reprocessing cycle of the endoscope has terminated, the case is extracted, with the endoscope inside it, from the seating of the machine and taken by hand to the place where it will be used.

The case with the endoscope can reach an overall weight of about 8 kilos or more, therefore transporting it by hand can be difficult, given that in hospital buildings of average to large size, the machine can be several hundred meters away from where the endoscope will be used.

The maneuvers for inserting and removing the case with the endoscope into and from the seating can also be inconvenient and laborious, since the case has to be lifted to insert it into and remove it from the seating precisely.

Another negative feature is that the removal or insertion of the endoscope from and into the case requires not only the sliding guides, but also a free support plane for the stable positioning of the case.

One purpose of the present invention is to obtain a machine for reprocessing an endoscope that allows to facilitate the transport of the endoscope to the various places where it is used.

Another purpose of the present invention is to obtain a machine for reprocessing an endoscope that guarantees the sterility of the endoscope contained in the chamber after reprocessing, even during transport to the places where it is used.

Another purpose of the present invention is to obtain a machine for reprocessing an endoscope that is simple and economical to obtain.

The Applicant has devised, tested and embodied the present invention to overcome the shortcomings of the state of the art and to obtain these and other purposes and advantages.

SUMMARY OF THE INVENTION

The present invention is set forth and characterized in the independent claims, while the dependent claims describe other characteristics of the invention or variants to the main inventive idea.

In accordance with the above purposes, a sterilization machine for reprocessing an endoscope according to the present invention comprises a fixed part and a mobile part, able to be taken close to, distanced from and reciprocally coupled with the fixed part.

According to one feature of the present invention, the fixed part comprises a first frame and at least part of a first fluid-dynamic circuit to feed and/or discharge fluids.

The first fluid-dynamic circuit is mounted on the first frame and is provided with a plurality of first connectors.

According to another feature of the invention, the mobile part comprises a tank suitable to receive the endoscope to be reprocessed, a lid to hermetically close the tank and a second fluid-dynamic circuit connectable to the endoscope and provided with second connectors able to be selectively coupled removably with the first connectors to achieve the fluidic connection with the first fluid-dynamic circuit.

According to another feature of the present invention, the mobile part comprises a second frame configured to support at least the tank, the second fluid-dynamic circuit and the second connectors.

In some forms of embodiment, the second frame is provided with rolling means for the selective movement of the second frame.

According to another feature, the first frame and the second frame comprise both guide means to guide the movement of the second frame close to the first frame, and to allow the connection of the first connectors with the second connectors, and also anchoring means to removably anchor the first frame to the second frame.

The rolling means allow to distance the mobile part and bring it close to the fixed part, while the guide means and the anchoring means guarantee easy engagement and dis-engagement of the mobile part with respect to the fixed part.

The possibility of transferring the mobile part from the fixed part to the place where the endoscope will be used, and vice versa, without having to make any lifting effort, is particularly advantageous, since the mobile part slides thanks to the rolling means.

The same considerations also apply to the steps of engaging and dis-engaging the mobile part with and from the fixed part. Indeed, during these operations too, the mobile part can easily be drawn thanks to the rolling means, and it will be particularly simple to guide the mobile part toward the fixed part by means of the guide means and to anchor the second frame to the first frame by means of the anchoring means.

To couple the mobile part with the fixed part it is sufficient to bring these close to each other, using the guide given by the guide means and subsequently, by means of the anchoring means, to anchor the second frame to the first frame.

Furthermore, the second frame in itself supplies a support for the tank and the lid, which makes it unnecessary to have a support plane for the endoscope in the place where it will be used.

The same applies when the endoscope has to be disposed in the tank before it is reprocessed. The known solutions described above instead provide that the case must necessarily rest on a free support plane.

According to a preferred form of embodiment, the second frame develops vertically so as to facilitate access of an operator to the tank.

Preferably, the tank can be disposed at a height comprised between 100 cm and 150 cm. For this purpose, the second frame can be telescopic.

BRIEF DESCRIPTION OF THE DRAWINGS

These and other characteristics of the present invention will become apparent from the following description of some forms of embodiment, given as a non-restrictive example with reference to the attached drawings wherein.

To facilitate comprehension, the same reference numbers have been used, where possible, to identify identical common elements in the drawings. It is understood that elements and characteristics of one form of embodiment can conveniently be incorporated into other forms of embodiment without further clarifications.

DETAILED DESCRIPTION OF SOME FORMS OF EMBODIMENT

Figure 1:
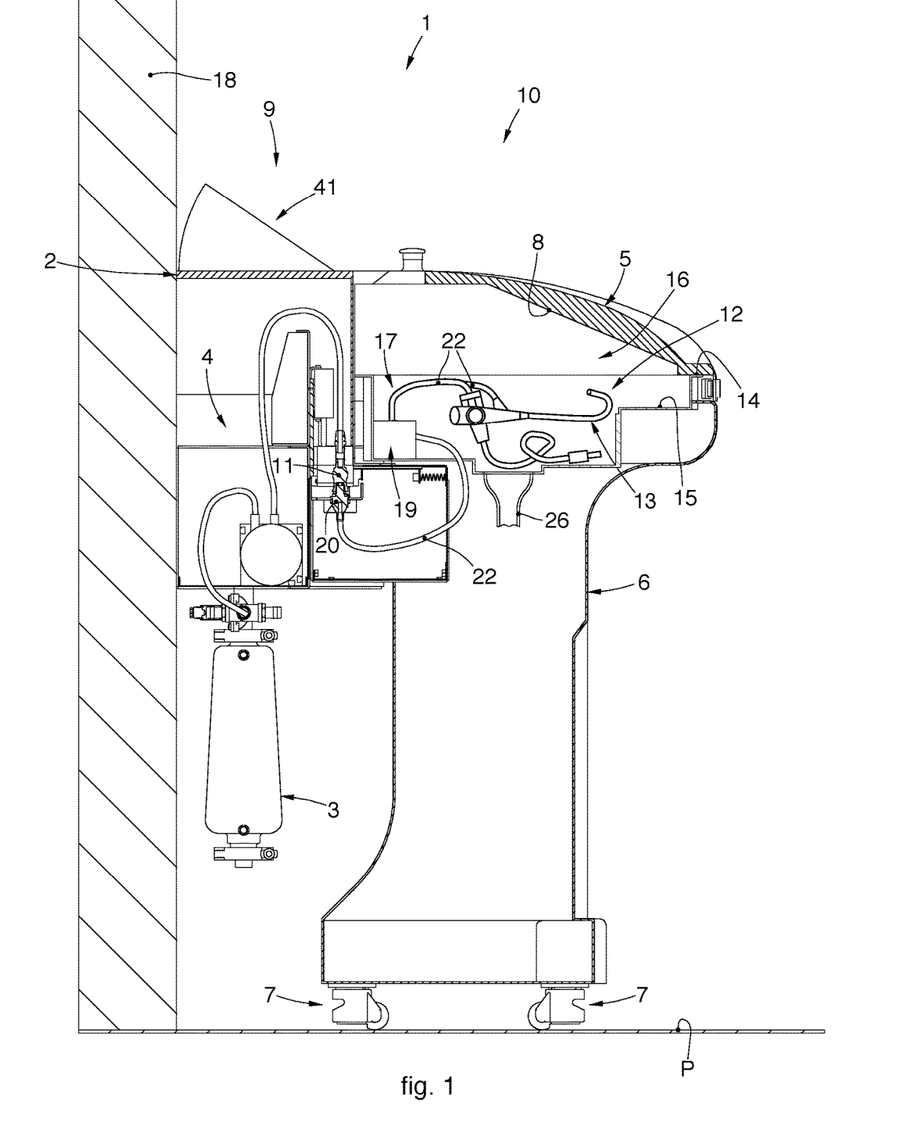
FIG. 1 is a section view of a sterilization machine for reprocessing an endoscope according to possible forms of embodiment.
Figure 2:
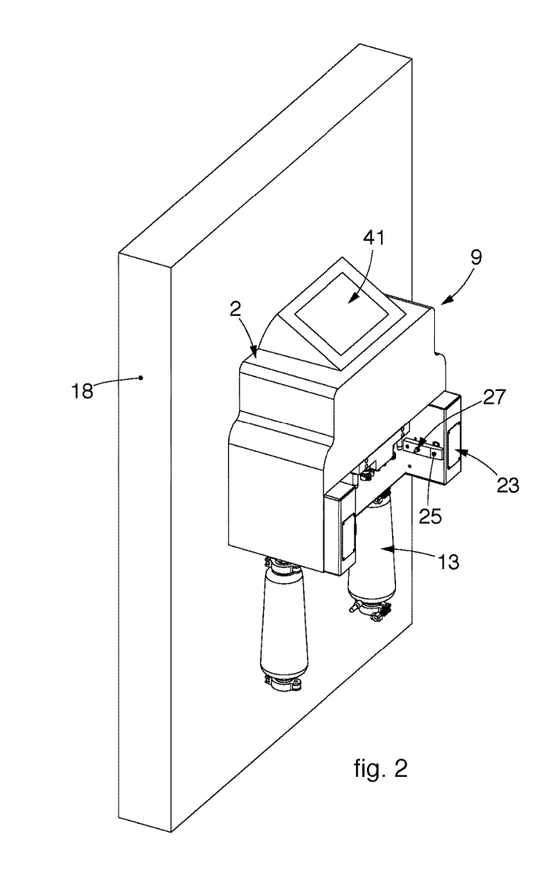
FIG. 2 is a perspective view of a part of the machine in FIG. 1.

With reference to FIG. 1, a sterilization machine for reprocessing an endoscope according to the present invention is indicated in its entirety by the reference number 1.

The sterilization machine 1 comprises at least a fixed part 9 and a mobile part 10 for containing at least one endoscope 13.

The mobile part 10 can be moved reciprocally close to or away from the fixed part 9 and is selectively able to be coupled with the latter.

The fixed part 9 comprises a fixed first frame 2 on which at least a part of the first fluid-dynamic circuit 4 is mounted, for feeding and/or discharging fluids.

Some forms of embodiment of the present invention can provide that the first fluid-dynamic circuit 4 is connectable to at least one of either a plant for feeding washing liquid, a plant for feeding additives, a plant for introducing compressed gas, a drying plant, a sterilization plant.

According to possible forms of embodiment, injection means 3 can be mounted on the first frame 2, for the controlled injection of fluids into the first fluid-dynamic circuit 4.

The injection means 3 can comprise tanks for containing washing and/or sterilization fluids, pumping members, filters, command valves, safety valves or similar and comparable components.

According to some possible variant forms of embodiment, the injection means 3 can be separate elements from the first frame 2, mounted apart and connected for example by means of pipes to the first fluid-dynamic circuit 4.

According to possible forms of embodiment, the first fluid-dynamic circuit 4 can be provided with a plurality of first connectors 11 mounted on the first frame 2.

The first frame 2 can be installed on a supporting wall 18 or other similar or comparable support structure suitable for the purpose.

According to one possible form of embodiment, the mobile part 10 comprises a tank 12 provided with a cavity 15 suitable to receive the at least one endoscope 13 to be reprocessed.

The tank 12 is provided with at least one aperture 14 through which the endoscope 13 is inserted and removed.

The mobile part 10 also comprises at least one lid 5 suitable to close the tank 12 hermetically.

The lid 5 is provided with a wall 8, internal during use, which together with the cavity 15 and when the lid 5 is closed, defines a chamber 16 in which the washing, drying and/or sterilization of the endoscope 13 is carried out.

Figure 3:
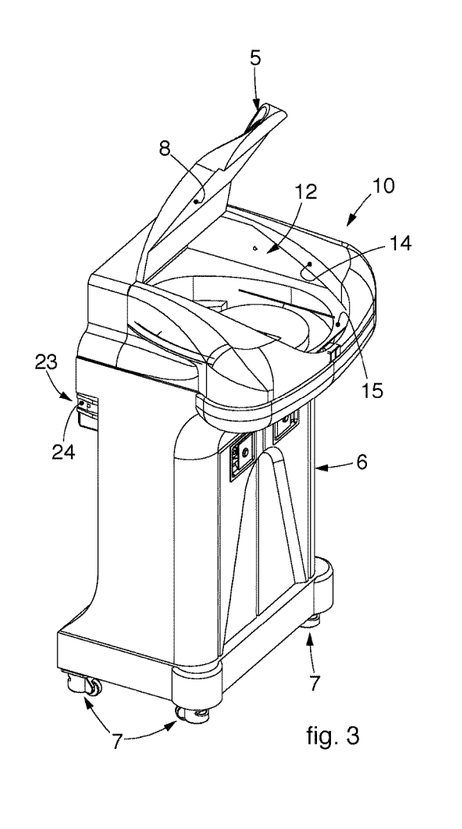
FIG. 3 is a perspective view of another part of the machine in FIG. 1.

The lid 5 is suitable to assume at least a first position, shown for example in FIG. 3, in which the tank 12 is accessible to introduce or remove the endoscope 13, and a second position, shown for example in FIG. 1, in which the wall 8 of the lid 5 and the cavity 15 of the tank 12 form said chamber 16.

The lid 5 can be hinged to the tank 12 so as to rotate, to move from the first position to the second position or vice versa.

The mobile part 10 comprises a second fluid-dynamic circuit 17 configured to be connected during use to the endoscope 13 and the tank 12.

According to possible forms of embodiment, the second fluid-dynamic circuit 17 can be disposed at least partly inside the tank 12 to allow it to be directly connected to the endoscope 13 by an operator.

In possible forms of embodiment, the second fluid-dynamic circuit 17 can comprise connection pipes 22, at least some of which are disposed inside the tank 12 and are able to be selectively coupled with connectors of the endoscope 13.

According to possible implementations, possibly combined with forms of embodiment described here, the second fluid-dynamic circuit 17 comprises connection means 19, for example sockets, disposed inside the tank 12 and to which the connectors of the endoscope 13 are connected.

The mobile part 10 comprises a second frame 6 configured to support at least the tank 12, the lid 5 and the second fluid-dynamic circuit 17.

The second frame 6 in itself supplies a support for the tank 12 and the lid 5: this makes it unnecessary to have a support plane in the place where the endoscope 13 will be used. The same applies when it is necessary to dispose the endoscope 13 in the tank 12 before it is reprocessed.

In possible forms of embodiment of the invention, it may be provided that the second frame 6 is made in a single body at least with the tank 12 containing the endoscope 13. This allows to obtain an extremely solid and resistant structure for movement.

In other forms of embodiment, it may be provided that the tank 12 is a separate element from the second frame 6 and subsequently mounted solidly on the latter. In this case suitable connection means may be provided between the tank 12 and the second frame 6, such as snap-in, bayonet or clip connection elements. This greatly simplifies the operations for making the second frame 6 and the tank 12.

Preferably, the second frame 6 develops vertically to facilitate access to the tank 12 by an operator. The second frame 6 can develop vertically so that the tank 12 reaches a height comprised between 100 cm and 150 cm with respect to a support plane P on which the second frame 6 is mobile.

According to possible forms of embodiment, the second frame 6 has a telescopic configuration to vary at least the positioning height of the tank 12 with respect to the support plane P, for example to adapt it to the requirements of the operator or to allow the coupling of the mobile part 10 to the fixed part 9 as will be described hereafter.

According to one form of embodiment of the present invention, the second frame 6 is provided with rolling means 7 to move the mobile part 10. In particular, the rolling means support the second frame 6 and allow it to slide on the support plane P.

The rolling means 7 can comprise wheels, bearings or similar components suitable for the purpose.

In the form of embodiment shown in FIGS. 1 and 3, the rolling means 7 comprise wheels constrained to the lower part of the second frame 6.

The rolling means 7 allow to distance the mobile part 10 from, and bring it close to, the fixed part 9. In this way the mobile part 10 can be transferred from the fixed part 9 to the place where the endoscope 13 will be used, and vice versa, without having to make any lifting effort.

The second fluid-dynamic circuit 17 is provided with a plurality of second connectors 20 mounted on the second frame 6 and able to be selectively coupled removably with the first connectors 11 mounted on the first frame 2, to achieve the fluidic communication with the first fluid-dynamic circuit 4.

In this way, when the mobile part 10 is coupled with the fixed part 9, the first 4 and second fluid-dynamic circuits 17 can be connected to each other, allowing the process fluids to pass to and from the endoscope 13 and to and from the tank 12.

In particular, the first 4 and second fluid-dynamic circuits 17 are configured to allow the passage through them of at least one of either washing liquids, sterilization liquids, flushing gases or seal verification gases.

The first 4 and second fluid-dynamic circuits 17 can also be configured to allow to discharge washing liquids present in the tank 12, for example through a discharge pipe 26.

According to possible forms of embodiment, the second connectors 20 are mounted in a fixed position on the second frame 6, accessible from the first frame 2 and in particular from the first connectors 11.

According to one possible form of embodiment, the coupled condition of the mobile part 10 with the fixed part 9 also determines a corresponding connection action between the first connectors 11 and the second connectors 20.

Possible forms of embodiment of the present invention (FIGS. 1, 5, 6 and 7) provide that the first connectors 11 and second connectors 20 are mounted according to a vertical orientation in order to allow the spontaneous drainage, through gravity, of possible liquids that can remain in the pipes or connection portions once the first connectors 11 are disconnected from the second connectors 20.

According to one solution of the present invention (FIGS. 4, 6, 7 and 8), the second frame 6 can be provided with a covering body 32, configured to protect the second connectors 20 and close them with respect to the external environment at least when the mobile part 10 is not coupled with the fixed part 9.

Figure 4:
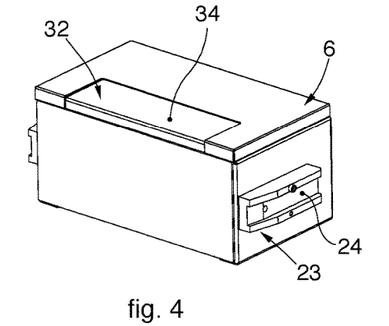
FIG. 4 is a view of a component of the part shown in FIG. 3, according to a possible form of embodiment.
Figure 6:
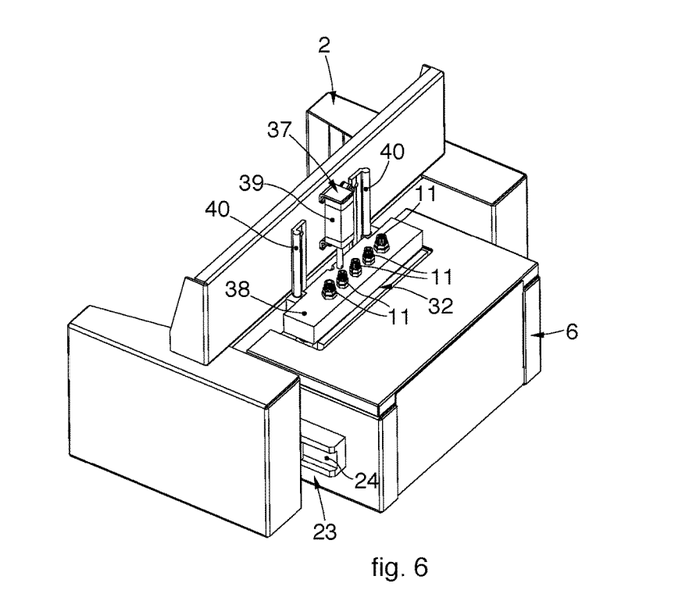
FIG. 6 is a perspective view of the components in FIGS. 4 and 5 in an assembled condition.
Figure 7:
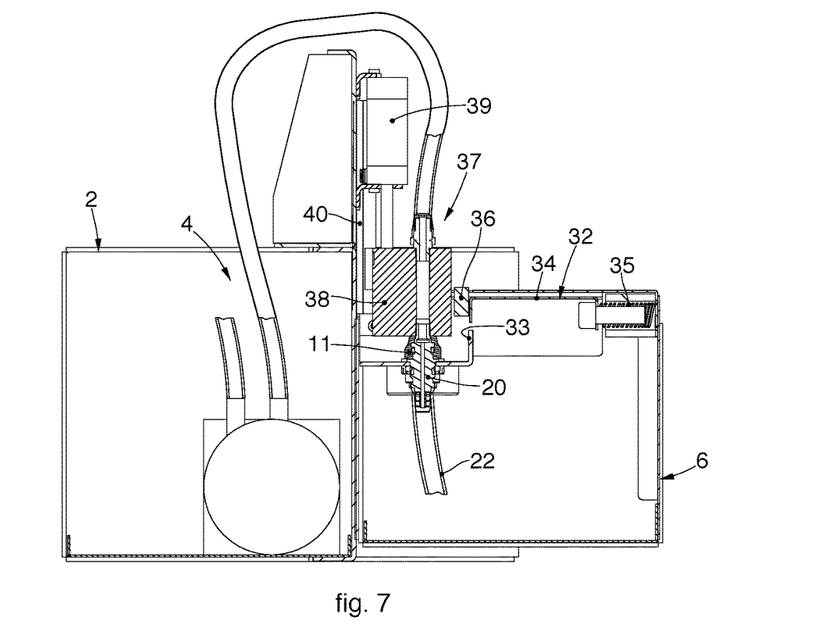
FIG. 7 is a view of a cross section of FIG. 6.

According to the form of embodiment shown in FIGS. 4, 6 and 7, the second connectors 20 are mounted in a containing compartment 33, provided in the second frame 6, selectively openable or closable by means of the covering body 32.

The covering body 32 can comprise a plate 34 mounted sliding on the second frame 6, and retaining members 35 configured to keep the plate 34 in a position of normal closure of the containing compartment 33.

The first frame 2 is in turn provided with a protruding portion 36, suitable to contact the covering body 32 when the mobile part 10 is coupled with the fixed part 9, and to determine the opening of the containing compartment 33.

Figure 5:
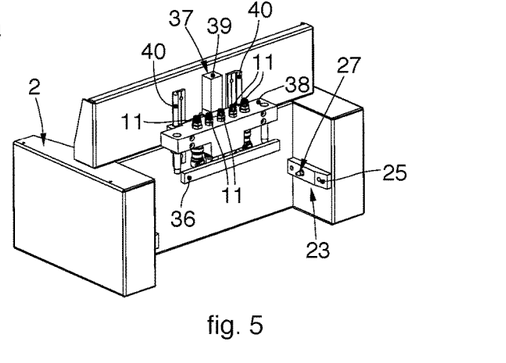
FIG. 5 is a view of a component of the part shown in FIG. 2, according to a possible form of embodiment.

In possible forms of embodiment, the first connectors 11 can be mounted on a positioning member 37 configured to take the first connectors 11, when the mobile part 10 is coupled to the fixed part 9, to a first connection position with the second connectors 20, and a second position in which there is no coupling and no reciprocal interference.

The positioning member 37 may comprise, merely by way of example, a support body 38 on which the first connectors 11 are mounted, and an actuator 39 configured to move the support body 38 and take the first connectors 11 to the first or second position.

According to possible forms of embodiment, the positioning member 37 may also comprise guide elements 40, configured to guide the movement of the support body 38.

At least one of either the first frame 2 or the second frame 6, or both, comprise guide means 23 (FIGS. 2-6) configured to guide the reciprocal coupling of the mobile part 10 with the fixed part 9 and to guarantee the precise positioning thereof.

In particular, the guide means 23 are configured to dispose at least the second connectors 20 present in the second frame 6 in a position suitable for them to connect with the first connectors 11 of the first frame 2.

The guide means 23 can comprise, for example, at least a guide bar 25, in this case two guide bars 25, attached on the first frame 2, and at least a shaped section bar 24, in this case two shaped section bars 24, attached on the second frame 6 and suitable to reciprocally couple with the guide bars 25.

According to a possible form of embodiment, the shaped section bars 24 and the guide bars 25 are mounted respectively on the first frame 2 and the second frame 6, at the same height as the support plane P on which the mobile part 10 is made to slide. This allows a reciprocal coupling of the mobile part 10 with respect to the fixed part 9 simply by being brought close to it.

According to possible forms of embodiment of the present invention, the mobile part 10 and the fixed part 9 comprise anchoring means 27 (FIG. 8), configured to removably constrain the first frame 2 with respect to the second frame 6 when the fixed part 9 and the mobile part 10 are coupled.

Figure 8:
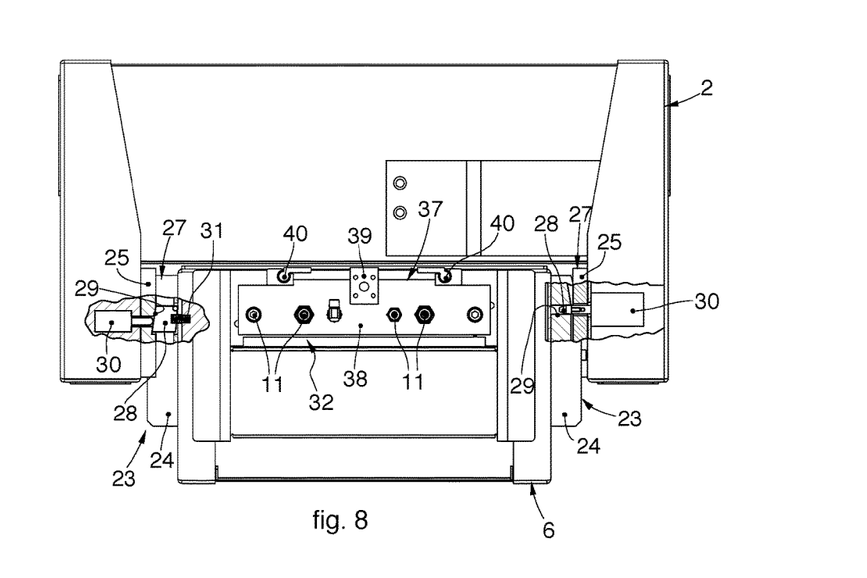
FIG. 8 is a plan view of FIG. 6.

According to possible forms of embodiment, the anchoring means 27 may comprise snap-in elements, retaining elements, elastic elements or actuator members.

With reference to FIG. 8, we shall now describe possible forms of embodiment in which the anchoring means 27 can comprise interference elements 28 able to be selectively coupled with mating housing seatings 29 made respectively on the first frame 2 and the second frame 6 or vice versa. De-activation members 30 are provided to reciprocally de-couple the interference elements 28 from the housing seatings 29 at least when the mobile part 10 is required to be de-coupled from the fixed part 9.

FIG. 8 shows two possible forms of embodiment of the anchoring means 27 between the fixed part 9 and the mobile part 10.

In particular, the anchoring means 27, shown on the left in FIG. 8, comprise an interference element 28 with a conical configuration mounted on the second frame 6 and kept in a normally protruding position with respect to the second frame 6 by an elastic element 31.

The interference element 28 can be mounted in correspondence with the guide means 23 and protruding with respect to the shaped section bar 24.

The housing seating 29 is made on the first frame 2, in correspondence with the guide means 23, and is configured to allow to house the interference element 28.

The housing seating 29 can be made for example directly on the guide bar 25.

The de-activation member 30 is also mounted on the first frame 2, in a position suitable to release the interference element 28 from the housing seating 29.

The de-activation member 30 may comprise for example a pneumatic or electric piston, configured to thrust the interference element 28 and cause it to return.

The anchoring means 27 shown on the right in FIG. 8 on the contrary comprise a housing seating 29 made in the second frame 6.

Instead, on the first frame 2, a de-activation member 30 is provided on which the interference element 28 is mounted.

The de-activation member 30 selectively activates or de-activates the interference element 28 in the housing seating 29.

According to possible forms of embodiment of the present invention, the fixed part 9 and the mobile part 10 can each be provided with respective electric connection elements, able to be selectively coupled with each other when the mobile part 10 is coupled with the fixed part 9.

The electric connection elements can be configured to supply electric power, for example to pressure sensors, temperature sensors, humidity sensors, or to breakdown detectors, to indicators of the functioning state of the machine 1, for example to indicate on the mobile part 10 the state of reprocessing of the endoscope 13 under way.

In possible forms of embodiment, the electric connection elements can be provided to activate/de-activate closing and clamping elements, electrically activated, of the lid 5 with respect to the tank 12.

According to possible forms of embodiment, the mobile part 10 and the fixed part 9 can be provided with respective closing means, activated mechanically, and configured to constrain the position of the lid 5 so as to prevent it from opening.

The closing means may comprise actuation rods, reciprocal contrast elements, elastic elements, constraint seatings and possible combinations of the above.

The fixed part 9 can comprise control and management means 41 (FIGS. 1 and 2), possibly governed by user interface means, and configured to control and manage the washing process of the endoscope 13.

It is clear that modifications and/or additions of parts may be made to the sterilization machine 10 as described heretofore, without departing from the field and scope of the present invention.

It is also clear that, although the present invention has been described with reference to some specific examples, a person of skill in the art shall certainly be able to achieve many other equivalent forms of sterilization machine 10, having the characteristics as set forth in the claims and hence all coming within the field of protection defined thereby.

The invention claimed is:

1. Sterilization machine for reprocessing an endoscope comprising a fixed part and a mobile part, able to be taken close to, distanced from and reciprocally coupled with said fixed part, said fixed part comprising a first frame and at least part of a first fluid-dynamic circuit for feeding and/or discharging fluids, mounted on said first frame and provided with a plurality of first connectors and said mobile part comprising a tank-suitable to receive the endoscope to be reprocessed, a lid to hermetically close said tank and a second fluid-dynamic circuit connectable to said endoscope and provided with second connectors, able to be selectively coupled removably with said first connectors so as to achieve the fluidic communication with the first fluid-dynamic circuit, wherein said mobile part comprises a second frame configured to support at least said tank, said second fluid-dynamic circuit and said second connectors, in that said second frame is provided with rolling means to move it, and in that said first frame and said second frame comprise guide means to guide the movement of the second frame close to the first frame and to allow the connection of the first connectors with the second connectors, and anchoring means to removably anchor the first frame to the second frame, and wherein said second frame develops vertically to facilitate access to said tank by an operator.

2. Machine as in claim 1, wherein injection means are mounted on said first frame, for the controlled injection of said fluids into the first fluid-dynamic circuit and the second fluid-dynamic circuit.

3. Machine as in claim 1, wherein said second fluid-dynamic circuit is disposed at least partly inside said tank, to allow a direct connection thereof to the endoscope by an operator.

4. Machine as in claim 1, wherein said second frame is made in a single body at least with said tank.

5. Machine as in claim 1, wherein said tank is a separate element from the second frame, and in that reciprocal connection means are provided between said tank and said second frame for their reciprocal connection.

6. Machine as in claim 1, wherein said second frame develops vertically so that the tank reaches a height comprised between 100 cm and 150 cm with respect to a support plane on which said second frame is mobile.

7. Machine as in claim 1, wherein said second frame is provided with a covering body configured to protect said second connectors and to close them with respect to the external environment at least when said mobile part is not coupled with said fixed part.

8. Machine as in claim 7, wherein said second connectors are mounted in a containing compartment provided in the second frame and selectively openable or closable by said covering body.

9. Machine as in claim 1, wherein said first connectors are mounted on a positioning member configured to take said first connectors, when said mobile part is coupled with said fixed part, to a first connection position with said second connectors, or a second position of non-coupling and reciprocal non-interference.

10. Machine as in claim 1, wherein said anchoring means comprise interference elements able to be selectively coupled with mating housing seatings made respectively on said first frame and said second frame or vice versa, and de-activation members provided to reciprocally de-couple said interference elements from said housing seatings.

11. Machine as in claim 1, wherein said fixed part and said mobile part are each provided with respective electric connection elements, able to be selectively coupled with each other when said mobile part is coupled with said fixed part.

12. Sterilization machine for reprocessing an endoscope comprising a fixed part and a mobile part, able to be taken close to, distanced from and reciprocally coupled with said fixed part, said fixed part comprising a first frame and at least part of a first fluid-dynamic circuit for feeding and/or discharging fluids, mounted on said first frame and provided with a plurality of first connectors and said mobile part comprising a tank suitable to receive the endoscope to be reprocessed, a lid to hermetically close said tank and a second fluid-dynamic circuit connectable to said endoscope and provided with second connectors, able to be selectively coupled removably with said first connectors so as to achieve the fluidic communication with the first fluid-dynamic circuit, wherein said mobile part comprises a second frame configured to support at least said tank, said second fluid-dynamic circuit and said second connectors, in that said second frame is provided with rolling means to move it, and in that said first frame and said second frame comprise guide means to guide the movement of the second frame close to the first frame and to allow the connection of the first connectors with the second connectors, and anchoring means to removably anchor the first frame to the second frame, and wherein said second frame has a telescopic configuration so as to vary at least the positioning height of said tank with respect to a support plane on which said second frame is mobile.

* * * * *